(12) United States Patent
Chang

(10) Patent No.: US 11,379,760 B2
(45) Date of Patent: Jul. 5, 2022

(54) SIMILARITY BASED LEARNING MACHINE AND METHODS OF SIMILARITY BASED MACHINE LEARNING

(71) Applicant: Yang Chang, Methuen, MA (US)

(72) Inventor: Yang Chang, Methuen, MA (US)

( * ) Notice: Subject to any disclaimer, the term of this patent is extended or adjusted under 35 U.S.C. 154(b) by 788 days.

(21) Appl. No.: 16/275,681

(22) Filed: Feb. 14, 2019

(65) Prior Publication Data

US 2020/0265340 A1     Aug. 20, 2020

(51) Int. Cl.
| | |
|---|---|
| *G06N 20/10* | (2019.01) |
| *G16H 50/70* | (2018.01) |
| *G06N 20/00* | (2019.01) |
| *G06N 5/04* | (2006.01) |

(52) U.S. Cl.
CPC ............. *G06N 20/10* (2019.01); *G16H 50/70* (2018.01); *G06N 5/04* (2013.01); *G06N 5/047* (2013.01); *G06N 20/00* (2019.01)

(58) Field of Classification Search
CPC ........ G06N 20/00; G06N 20/10; G06N 20/20; G06N 5/04; G06N 5/047; G16H 50/00; G16H 50/20; G16H 50/30; G16H 50/50; G16H 50/70; G16H 80/00
See application file for complete search history.

(56) References Cited

U.S. PATENT DOCUMENTS

| | | | |
|---|---|---|---|
| 7,580,947 B2 | 8/2009 | Kasravi et al. | |
| 7,840,060 B2 | 11/2010 | Podilchuk | |
| 8,515,680 B2 | 8/2013 | Pipke et al. | |
| 9,251,029 B2 | 2/2016 | Otsuka et al. | |
| 9,323,886 B2 | 4/2016 | Fukushige et al. | |
| 9,349,105 B2 | 5/2016 | Beymer et al. | |
| 2004/0076984 A1 | 4/2004 | Eils | |
| 2009/0204551 A1 | 8/2009 | Wang et al. | |
| 2015/0039538 A1 | 2/2015 | Hefeeda et al. | |
| 2015/0169794 A1 | 6/2015 | Maennel | |
| 2015/0286955 A1* | 10/2015 | Virkar | G06N 20/10 706/12 |
| 2015/0317344 A1 | 11/2015 | Birdwell et al. | |
| 2017/0249559 A1 | 8/2017 | Herzog | |
| 2017/0270534 A1* | 9/2017 | Zoldi | G06F 16/24578 |
| 2020/0019890 A1* | 1/2020 | Rossi | G06N 20/10 |
| 2021/0019342 A1* | 1/2021 | Peng | G06F 16/583 |

FOREIGN PATENT DOCUMENTS

| | | |
|---|---|---|
| WO | 2017095413 | 6/2017 |
| WO | 2017148266 | 9/2017 |

* cited by examiner

*Primary Examiner* — Shane D Woolwine
(74) *Attorney, Agent, or Firm* — Lambert Shortell & Connaughton; David J. Connaughton, Jr.; Justin P. Tinger

(57) ABSTRACT

In accordance with aspects and embodiments, an improved similarity based learning machine and methods of similarity based machine learning are provided. More specifically, the learning machines and machine learning methods of the present disclosure advantageously define subjects by attributes, assign a first similarity score to each of the subjects, from the first similarity score, calculate attribute scaling factors, and use the attribute scaling factors to generate an improved similarity score. In accordance with aspects and embodiments, the improved similarity scores may be used to improve machine learning.

17 Claims, 4 Drawing Sheets

SIMILARITY BASED LEARNING MACHINE AND METHODS OF SIMILARITY BASED MACHINE LEARNING

FIELD OF INVENTION

The present disclosure relates to an improvement in the functioning of a learning machine computer. More specifically, an improved supervised learning machine and improved methods of supervised machine learning are provided.

DESCRIPTION OF RELATED ART

Machine learning refers to a specialized computer system configured to progressively improve its performance on a specific task without having been explicitly programmed to perform the task. Supervised learning is a subset of machine learning and refers specifically to the field of machine learning where learning occurs from a set of inputs with corresponding known outputs known as "training data". A supervised learning machine generally relies on algorithms to build mathematical models of the training data such that learning machine, when presented with a new input, can rely on its prior experience and what it learned from the experience in order to make predictions on the outcome.

A fundamental objective learning machines is for them to perform accurately on new tasks after having experienced a set of training data. There a number of existing models that seek to provide methods by which a computer can engage in such supervised machine learning.

Many of these models can broadly be descried as kernel methods. Kernel methods are a class of algorithms used for pattern analysis, where the general task is to identify and study relationships in datasets. Kernel methods generate predictions for new inputs not in the training data by applying a similarity function, k, called a kernel, to the input and each of the training inputs. The learning machine then and generating the predicted output by computing a weighted sum of the similarities of the new input's similarities to the training data's inputs and outputs.

For example, support vector machines (SVMs) are a set of supervised learning machines that can be viewed as a special case of kernel methods. SVMs are used for classification and regression. SVMs thus take training sets and build models that predict, in the case of classification, whether a new example falls into one category or another. In non-binary models, SVMs create regression algorithms to generate continuous outputs, and may be used for to predict values falling within a range, for example, price of an item over time.

Kernel method machines, as well as other types of learning machines, however have significant drawbacks. Existing supervised learning machines require large sets of training data on the order of billions of data points. Existing learning machines and methods of machine learning are thus unable to be used in fields where only a small set of training data is available, for example, where only 50 to a few hundred data points are available. The present disclosure advantageously provides learning machines and methods that do not require large training data to perform accurately.

Moreover, use of a large number of parameters or weights in a complex model can result in over-fitting. In other words, when the number of parameters is close, equal or more than the number of data points, such as in kernel methods on small sets of training data, model overfitting will occur and prediction accuracy of the machine learning may be reduced. Another way to characterize the overfitting is that while increasing complexity of the model reduces the training error, the model performs poorly when required to generalize. Thus while the training error decreases, the error between predicted outcomes when compared to actual, later-observed outcomes, increases. The present disclosure provides learning machines and methods that, even when presented with small training data, advantageously avoid overfitting. The learning machines and methods disclosed herein further improve upon existing similarly based learning machines.

Existing learning machines are often also sensitive to outliers. Moreover, existing learning machines often rely on assumptions made from distributions or correlation structures of the data for which accuracy cannot be assessed. Sensitivity to outliers and reliance on assumed characteristics of the training set may reduce the accuracy of predictions. The learning machines and methods described herein thus are not sensitive to outliers. Moreover, the machines and methods disclosed do not require assumptions to be made regarding the training data distribution or correlation structure, thereby improving the accuracy of predictions and enhancing learning.

SUMMARY OF INVENTION

In accordance with aspects and embodiments, a system for machine learning is provided, where the system comprises a computer and a computer-readable medium having software stored therein that when executed by said computer, performs a machine learning method comprising a computer-readable medium having software stored therein, when executed by said computer, performs a method comprising the steps of generating a similarix from received training data of N subjects, where each subject is defined by a set of attributes, assigning an initial similarity score for each of the subjects, calculating a scaling factor for each attribute, generating improved similarity scores using the scaling factors and using the improved similarity scores to predict future outcomes for new subject.

In accordance with aspects and embodiments, a method of supervised machine learning is provided comprising the steps of providing training data to a learning machine, generating initial similarity scores, generating improved similarity scores, using the improved similarity scores to model outcome, and using the modeled outcome to predict future outcomes.

In accordance with aspects and embodiments, a method of treating a disease in a current patient is provided, the method comprising the steps of providing training data of prior patients in a clinical trial to a learning machine, the training data including for each prior patient attributes and patient outcome, generating initial similarity scores between prior patients, generating improved similarity scores between prior patients, using the improved similarity scores to model patient outcome, using the modeled outcome to predict an outcome of a current patient, and using the predicted outcome to arrive at a course of treatment for the current patient.

DETAILED DISCLOSURE

Figure 1:
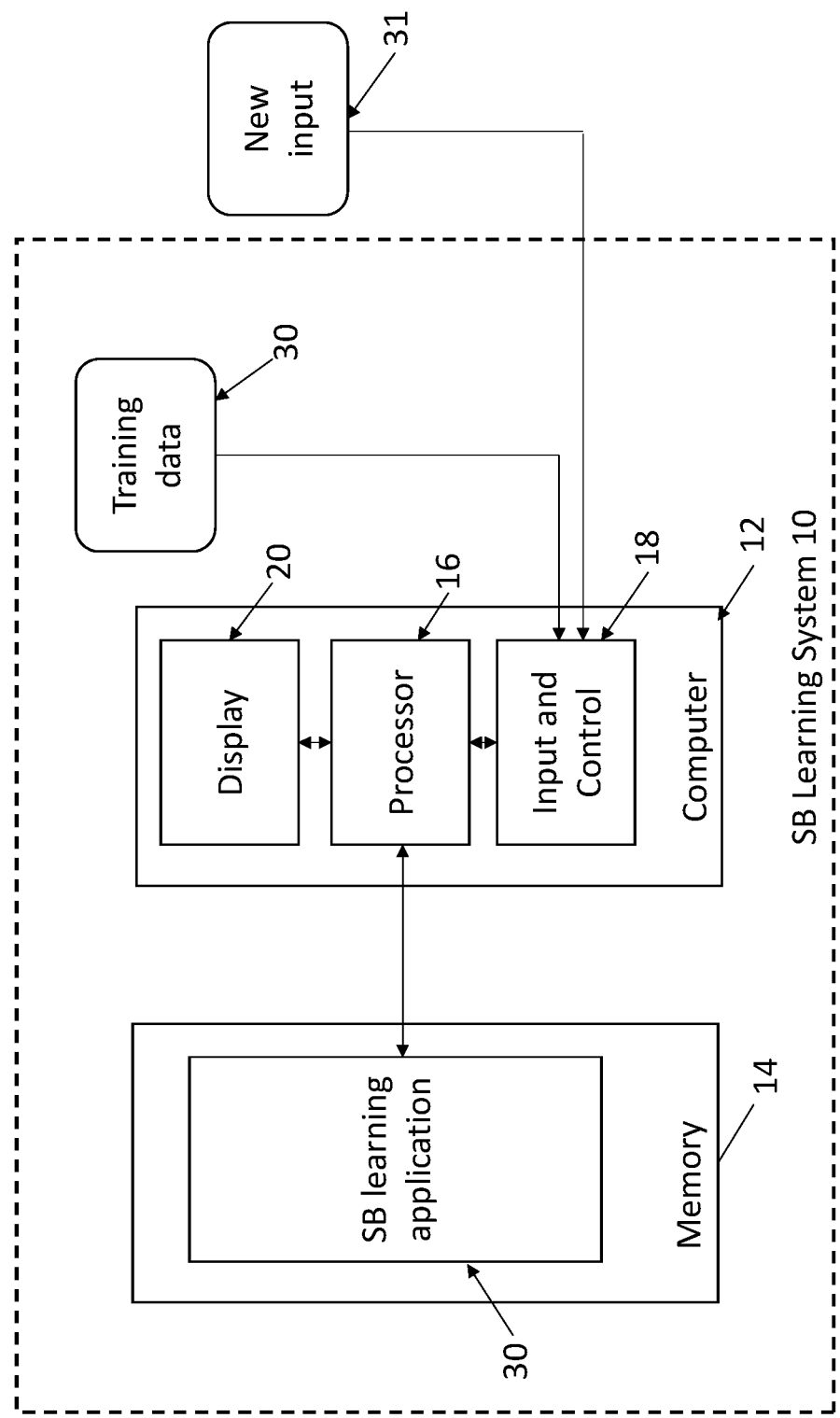
FIG. 1 provides a schematic representation of a similarity based learning machine in accordance with the present disclosure.

The detailed description set forth below in connection with the appended drawings is intended as a description of presently preferred embodiments of the invention and does not represent the only forms in which the present invention may be constructed and/or utilized. The description sets forth the functions and the sequence of steps for constructing and operating the invention in connection with the illustrated embodiments.

In the description, specific details are set forth in order to provide a thorough understanding of the examples disclosed. In other instances, well-known methods, procedures, components and materials have not been described in detail as not to unnecessarily lengthen the present disclosure.

The terminology used herein is for the purpose of describing particular embodiments only and is not intended to be limiting. As used herein, the singular forms "a", "an", and "the", are intended to include the plural forms as well, unless the context clearly indicates otherwise. It should be further understood that the terms "includes" and/or "including", when used in the present specification, specify the presence of stated features, integers, steps, operations, elements, and/or components, but do not preclude the presence or addition of one or more other features, integers, steps, operations, elements, components, and/or groups thereof not explicitly stated.

The present disclosure remedies problems with existing supervised learning machines and methods by providing learning machines and methods that more closely replicate the manner in which natural, human, learning occurs. Generally, human learning, i.e. prediction and decisions making, relies on the fundamental principal of similarity. Stated more explicitly, we learn by relying on our knowledge that similar things and individuals will behave similarly. The more similar they are, the more similar they will behave.

This principle is often used in scientific study. For example, no two individuals are in fact identical, but for the purposes of scientific study, similar individuals are often grouped together and considered approximately the same. This is often the case in pharmaceutical science, where individuals having the same disease, despite its progression being unique within each individual, are considered the same for the purposes of evaluating the efficacy of new drugs. Likewise, psychologists often study a group of people having similar personality traits or past experiences to explain and predict why people having similar personalities and/or past experiences behave in the manner they do. The similarities between things and events, that is, causal relationships in all forms, provide us with the ability to handle new and complex information by processing it with the limited ability of the human brain in accordance with reasonable predictions based on similar, previous, experiences.

This seemingly complicated description of how we learn is actually quite simple when put to practice. For example, people put to practice the idea of similarity each and every day: we know that objects with wheels tend to roll and move quickly and objects with sharp edges can be used for cutting. Another more nuanced example is the general believe that on every September 11$^{th}$, a terrorist attack is more likely in the United States. The present disclosure thus provides a method for machine learning whereby learning is accomplished by relying on similarities in much the same way as humans to learn.

FIG. 1 is a schematic representation of an exemplary embodiment of a similarity based (SB) learning system 10 in accordance with the present disclosure. The SB learning system 10 may include a computer 12 and a memory unit 14. Computer 12 may, for instance, be a typical digital computer that includes a central processor 16, an input and control unit 18 and a display unit 20. The central processor 16 may, for instance, be a well-known microprocessor. The input and control unit 18 may, for instance, be a keyboard, a mouse, a track-ball or a touch pad or screen, or some other well-known computer peripheral device or some combination thereof. The display unit 20 may, for instance, be a video display monitor, a printer or a projector or some other well-known computer peripheral device or some combination thereof.

The central processor 16 may have an internal data store and may also be connected to a computer readable medium, for example, an internal or external memory unit. The computer readable medium is shown in FIG. 1 as external memory unit 14. Computer readable medium 14 may be for instance, a hard drive, a tape drive, a magnetic storage volume or an optical storage volume or some combination thereof. The memory unit 14 may have store software and may for example store one or more machine learning applications 30. Control unit 18 may, for example, be used to input training data 22 into computer 12. Input and control unit 18 may further be used to cause processor 18 execute a machine learning application 30 having code stored in memory 14. Application 30 may then communicate with processor 16 such that processor 16 causes an output to be displayed on display 20. Input and control unit 18 may then, for example, be used to input new data into machine learning system 10 such that a predictive outcome from new data 31 is displayed on display 20.

Figure 2:
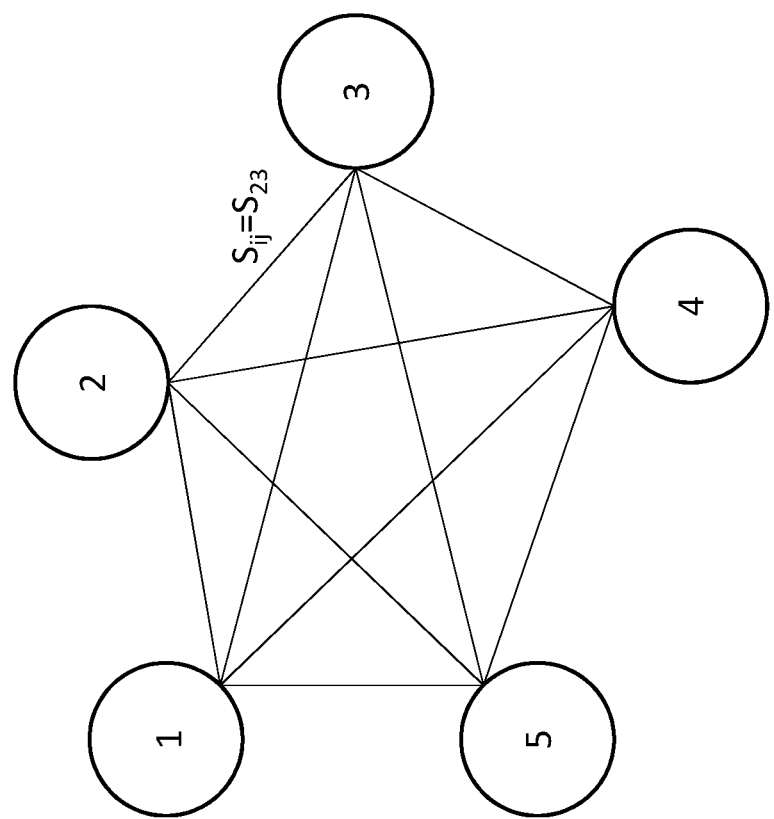
FIG. 2 provides a similarix in accordance with the present disclosure.

This similarity principle relied upon in the present disclosure can be described visually in what is called a similarix. An example of a five node similarix is shown in FIG. 2. Each of nodes 1-5 represents an object, person, subject, or event of interest. A node can thus be anything of import and is not limited to the examples recited herein. For simplicity, each node will be referred to hereinafter as representative of a subject, which may include, for example, a person. Each subject is connected to every other subject in the similarix by a line that represents the degree of similarity between the given node and every other node in the similarix. These lines may be referred to as links or edges in the similarix network and are assigned similarity scores representing degrees of similarity, denoted by $S_{ij}$ where i is a first subject and j is a second subject. Thus, the similarity score between paired subjects 2 and 3 is denoted by $S_{23}$.

Arriving at the similarity between two subjects first requires defining the subjects by characteristic variables, referred to herein as attributes. Each subject in the similarix will be defined by a set of attributes X. In an example where there are K attributes used to define each subject, each subject can be defined as the list of its attributes, such that a subject in the similarix can be represented be:

$$X_k, k=1,2,\ldots,K.$$

Thus based on the above, the i-th subject in a similarix of N subjects has the observed attributes:

$$X_{ik}, i=1,\ldots,N; k=1,2,\ldots,K.$$

In addition to having attributes, each subject in the simlarix is also associated with an outcome. Outcomes are dependent variables. That is, they depend upon the subject's attributes. The outcome of interest for i-th subject in the similarix is expressed as $O_i$.

It should be appreciated that even when two subjects have identical definitions within the similarix, that is, they possess identical attributes, they are not in fact identical. For example, if the subject is a person, each person in a given training data set will possess characteristics not captured by the selected attributes. Thus, while individuals in a clinical trial may be identical by the definitions with respect to selected attributes, and may for example be female, within a certain age range, and possess the same type of cancer, each person will still have a unique response to any administered therapies. In order to predict how a new female patient having the same cancer and within the same age range may respond to the therapy, a predictive model is used that weights a more similar person's outcome more heavily than a less similar person's outcome. For example, if the new patient has a given body mass index (BMI), the outcome of patients with BMIs falling within +/−25% of the new patient's BMI maybe weighted more heavily than the outcome of those patients having BMIs outside that range. Thus, for the j-th person having k attributes, the predicted outcome $Y_i$ for the i-th subject is the weighted outcomes of N people's outcomes $O_j$, j=1, 2, . . . , N from the training set:

$$Y_i = \sum_{j=1}^{N} W_{ij} O_j, i = 1, 2, \ldots, N \quad (1)$$

Where the weight, $W_{ij}$, depends on the similarly score $S_{ij}$ between the i-th and j-th subjects:

$$W_{ij} = \frac{S_{ij}}{\sum_{m=1}^{N} S_{im}} \quad (2)$$

A person, and more broadly, a node representing something of import, is defined by the selected attributes. Therefore, for given paired nodes, a different selection of attributes can lead to a different similarity score. Existing similarity based learning models do not provide meaningful ways to assign import to given attributes in calculating the similarity score. For example, in the Kernel models of the prior art, all attributes are considered to be of equal importance when arriving at a similarity score. Logic however tells us that that whether a person is male or female or if they are under 10 or over 70 are more significant attributes in assessing drug efficacy than, for example, a person's hair color.

In accordance with aspects and embodiments, an attribute-scaling factor for similarity-based machine learning is provided to improve performance. The attribute-scaling factor, also referring to herein as simply the scaling factor, scales, i.e., weights, relative importance of individual attributes within given similarity scores. Absent attribute scaling, it is difficult if not impossible to intelligently and objectively determine the relative importance of attributes. Moreover, similarity scores that do not consider the relative importance of selected attributes provide lesser quality information to the learning machine and thus result in inferior learning to the methods described herein.

The learning machines and methods of the present disclosure thus evaluate similarity on a plurality of levels, and most advantageously, are able to model similarity based on the relationship of independent variables or attributes to one another to generate a scaled similarity according to the significance of each independent variable on outcome. Because similarity between two subjects is also dependent on the outcome of interest, the similarity based leaning methods disclosed determine the attribute-scaling variables. It can thus be seen that similarity scores are also dependent outcomes from the training data. Thus the scaling factors and similarity scores are optimized. When making predictions, the scaled similarity scores are further normalized to obtain weights in training and prediction. In contrast, existing kernel methods model similarity directly such that the presence or absence of each attribute is considered equally relevant to outcome, and only unscaled similarity is used to predict outcomes. For example, existing methods define objects only in relation to how similar they are to one another based on a subjective judgment, which is not optimized based on the training data. A predictive outcome is achieved by using a pre-determined similarity function to weight all training data outcomes. These existing methods therefore prevent optimization of similarity scores and adversely affect the precision of prediction. Furthermore, these methods represented by kernel methods have serious overfitting problems due the larger number of weights or parameters need to be determined. In contrast, the present learning machines and machine learning methods determine similarity by a small set of attribute-scaling factors that are calculated through mathematical optimization. Individual similarity scores are optimized individually to improve predictive ability.

Thus, in accordance with aspects and embodiments, an improved method of determining a similarity score $S_{ij}$ is provided. The improved similarity score $S_{ij}$ is defined as a function of distance $d_{ij}$ between objects, and distance is a function of attribute scaling factor $R_k$ (k=1, 2, . . . , K) for the selected attributes, where K is the number of attributes.

Distance, also known as dissimilarity, between subjects i and j, is defined as $$d_{ij} = \left[ \sum_{k=1}^{K} (R_k |X_{jk} - X_{ik}|)^\rho \right]^{\frac{1}{\rho}}, R_k, k = 1, 2, \ldots, K; \rho = 1 \text{ or } 2 \quad (3)$$

Here, and as can be seen in equation (3), the scaling factor $R_k$ scales a given attribute k in the distance or similarity calculation.

The similarity score $S_{ij}$ can be expressed in three different way; as an exponential function, as logarithmic-like function, and as a distance-inverse function.

The similarity score $S_{ij}$ can be defined as the exponential function:

$$S_{ij} = \exp(-d_{ij}^\eta), \eta > 0 \quad (4)$$

Alternatively, the similarity score $S_{ij}$ can be defined as the logarithmic-like function:

$$S_{ij} = \frac{2}{1 + \exp(d_{ij}^\eta)}, \eta > 0 \quad (5)$$

Or, the similarity score $S_{ij}$ can be defined as the distance-inverse function:

$$S_{ij} = \frac{1}{1+d_{ij}^{\eta}}, \eta > 0 \quad (6)$$

The common requirements for a similarity function $S_{ij}$ ($d_{ij}$) are $S_{ij}(0)=1$ and $S_{ij}(\infty)=0$, where $d_{ij}$ is the distance between the two subjects.

Figure 3:
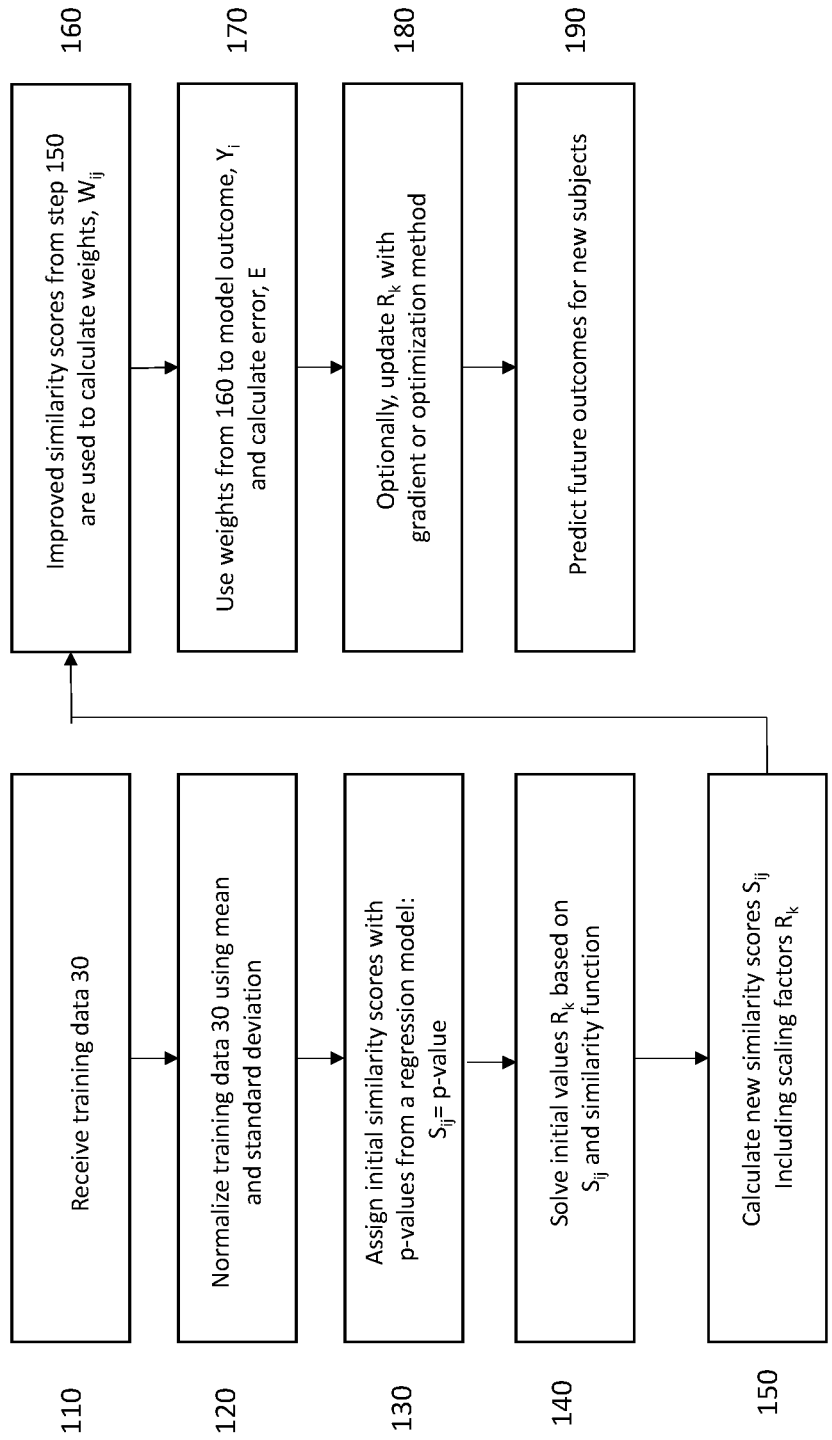
FIG. 3 provides a flow chart of an embodiment of the present disclosure.

Referring now to FIG. 3, the steps taken by the SB learning machine according with embodiments of the present invention will be described.

Prior to generating scaling factors or similarity scores, upon receiving training data in step 110, in step 120 the SB learning machine normalizes the dataset such that all variables have a mean of 0 and a standard deviation of 1. Normalization is achieved for each variable by subtracting its mean and then dividing by its standard deviation. Standardizing the training data enhances the SB learning of the present disclosure. Moreover, it ensures that private information, for example in the case of clinical trials, is removed from the dataset. Rather than the actual data, learning is performed on the data structure.

After standardization step 120, step 130 is performed to generate initial similarity scores. The initial similarity scores are generated such that initial scaling factors can be identified in step 140. Solving for initial scaling factors $R_k$ based on initial similarity provides an objective similarity score that may improve machine learning. This objective similarity score is referred to herein as an "improved" similarity score. Furthermore, The present method is advantageous over other methods in that if training data is limited, the method by which the scaling factors are generated can be tailored to accommodate limited training data having limited similarity scores available.

If, for example, very limited training data is available, prior knowledge of similarity scores between a small set of subjects can be relied upon to solve for the scaling factor $R=(R_1, R_2, \ldots R_k)$ in step 140 using the appropriate similarity function (Equations 4-6):

$$R=f(S), \text{ where } S=(S_1, S_2, \ldots, S_k).$$

Alternatively, when training data is available, scaling factors can be determined in step 140 by generating a statistical model from the data structure and assigning p-values to the initially generated similarity scores. The scaling factor, R, is then determined using the defined similarity function.

For example, when $\eta=1$ and $\rho=2$, the exponential similarity function (4) becomes:

$$S_{ij} = \exp\left(\sum_{k=1}^{K}(R_k|X_{jk}-X_{ik}|)^2\right), \quad (7)$$

When using p-values to determine $R_k$ in step 140, one can see that p-value $P_k$ can be interpreted as a similarity score and can replace $S_{ij}$ on the left side of Eq. 7. The similarity scores range from 0 (where the subjects are completely different) to 1 (where the subjects are identical) inclusively.

When for example a k-th pair of subjects have identical attributes under consideration with the exception of the k-th variable, the summation on the right side of Eq. 7 will disappear and the scaling factor $R_k$ with similarity score $P_k$ can be solved explicitly using Eq. 7. This enables the initial attribute-scaling factors to be determined, that is, $$R_k^0 = \frac{\ln(P_k)}{|X_{jk}-X_{ik}|}, k=1, 2, \ldots, K \quad (8)$$

Where the superscript "0" is used to indicate the initial value of R, $|X_{jk}-X_{ik}|$ is the distance between the $1^{st}$ and third quartiles, which can be considered the difference between two typical subjects in the data regarding this variable.

After $R_k$ are determined in step 140, the values are used in step 150 and re-inserted into in Eq. 7 to calculate new similarity scores $S_{ij}$ that include the scaling factor, $R_k$. Upon completion of step 150, the obtained scaled similarity scores are used in Eq. 2 to calculate weights $W_{ij}$ in step 160, which in turn can be used to model outcome, $Y_i$, in step 170. The scaling factors and similarity scores can be further improved using the gradient method or optimization, in step 180, using Eqs. 9 through 13. Modeled outcome 190 can be used to predict new outcomes in step 190.

In accordance with the disclosure, new outcomes are predicted by normalizing new data using the mean and standard deviation from the training set. Similarity scores $S_{ij}$ are calculated between the new subjects and the training subjects using the calculated scaling factor, $R_k$, and outcomes can be predicted using Eq. 1.

In accordance with embodiments of the disclosure, missing data may be handled in one of two ways. Missing data refers to data missing from the training set with respect to the attributes of subjects within the set. If, for example, some attributed are not collected for some subjects, the missing data can be handled by excluding the missing attributes in the calculation of similarity scores for the subject. Alternatively, the mean, median, or mode of the attributes collected for the subject can be used to generate similarity scores between the subject and others in the training set for which all attributes are collected.

In accordance with aspects and embodiments of the disclosure, the similarity based learning machines of the present invention may update and/or tune the attribute scaling factors $R_k$ as learning proceeds, shown as step 180 in FIG. 3. The present similarity based learning machines thus have two methods for such refinement: a gradient method and an optimization method.

In the gradient method of the present disclosure, the modification of attribute scaling factors is a function of the initial value of $R_k$, $R_x^0$, the learning rate $\alpha$, and the mean square error E of the training set:

$$R_k^1 = R_k^0 - \alpha\frac{\partial E}{\partial R_k} \quad (9)$$

Where the mean square error E for the training set is:

$$E = \frac{\sum_{i=1}^{N}(Y_i-O_i)^2}{N} = \frac{1}{N}\sum_{i=1}^{N}\left(\sum_{J=1}^{N}W_{ij}O_J - O_j\right)^2 \quad (10)$$

While the learning rate can be selected based on a plurality of factors, in accordance with aspects and embodiments, the learning rate $\alpha$ is expressed as:

$$\alpha = \frac{b\|R\|}{\left\|\frac{\partial E}{\partial R}\right\|} = \frac{b\sqrt{\sum_k^K R_k^2}}{\sqrt{\sum_k^K \left(\frac{\partial E}{\partial R_k}\right)^2}} \qquad (11)$$

Where b is a small value in the rage 0 to 1, representing percent in error reduction.

In accordance with other embodiments, the attribute scaling factors may be adjusted by an optimization method. In the optimization method, a penalty is imposed on larger R values to avoid over-fitting of data. Thus, the following loss function L is used to solve for R such that L is minimized:

$$L = E + \lambda \|R\|_2 \qquad (12)$$

Where $\lambda > 0$ and is a small positive value.

By taking the partial derivative of Eq. 12 with respect to $R_k$, the following is obtained:

$$\frac{\partial}{\partial R_k}\left\{E + \lambda \sum_{k=1}^{K} R_k^2\right\} = 0 \qquad (13)$$

From equation 13, a new, optimized, $R_k$ can be obtained.

In accordance with aspects and embodiments of the present disclosure, a sequential SB learning machine is provided. Sequential machine learning in general provides improvements over non-sequential machine learning. In sequential machine learning, training takes place over time and predicted outcomes are compared to those collected as observed, In accordance with the sequential SB learning machines of the present invention, sequential SB machines use the same learning as described herein but learning additionally includes comparing observed outcomes to predicted outcomes over time. The sequential learning machines and methods of the present disclosure thus enable the attribute scaling factors of the present disclosure to be continuously updated as data accumulates.

The SB and sequential SB learning machines of the present invention can be further specified to learn different outcome variables. For example, in binary outcome sequential SB learning, that is, where the task has a yes/no answer, dependent variables can be coded as either 0 or 1 and no standardization of data is needed. All independent variables should be standardized. For learning binary outcome tasks in accordance with the present disclosure, similarity scores can simply be generated from the p-values obtained from multivariate logistic regression.

For SB and sequential SB leaning tasks wherein the outcome is a nominal variable, when determining the scaling factors using the training data, including the data of observed outcomes collected over time, the error is 0 if the modeled outcome is the same as the observed outcome O. If the modeled outcome Y is different from the observed outcome O, the error is 1. Scaling factors are updated in accordance with the scaling methods described herein for continuous outcome variables and include the gradient and the optimization methods disclosed.

For SB and sequential SB learning tasks having multiple outcomes, such as survival time (t) and quality of life score (q), as may be used in clinical trials, an outcome vector (O) can be used, in which each component of the vector is an outcome parameters:

$$O = \{t, q\}$$

For the i-th subject, the observed outcome is denoted by $O_i$ and the corresponding modeled outcome is denoted by $Y_i$. The predictive error E for such multiple outcomes is defined as:

$$E = \frac{\sum_{i=1}^{M}(Y_i - O_i)^T C(Y_i - O_i)}{M} \qquad (14)$$

Where C is a matrix wherein the elements measure the relative importance of different outcomes, whereas the scaling factors measure the relative importance in contributing to the outcome can either the same or different for different outcomes for a given subject. The determination of the attribute-scaling factors is identical to the continuous, single outcome variable model, using either the gradient method (Eq. 9) or the optimization method (Eq. 13) and the error E from Eq. 14.

In accordance with aspects and embodiments, the SB learning machines of the disclosure may perform recursive hierarchical learning. Recursive hierarchical learning, in general, a learning model designed to replicate natural human learning. Humans learn not in absolutes, but with an accepted tolerance for certain outcomes. For example, no two individuals sound identical when speaking and thus for every word learned, the human brain recognizes the word with a certain tolerance level that accounts for the differences in how speech sounds from one person to another. Thus, learning is performed is with some tolerance for ambiguity; a given word may sound different when spoken by different people, but the human brain accepts the ambiguities and differences and recognizes the word regardless of who says it. Recursive hierarchical learning seeks to include tolerance for ambiguity in the predicting of outcomes.

Figure 4:
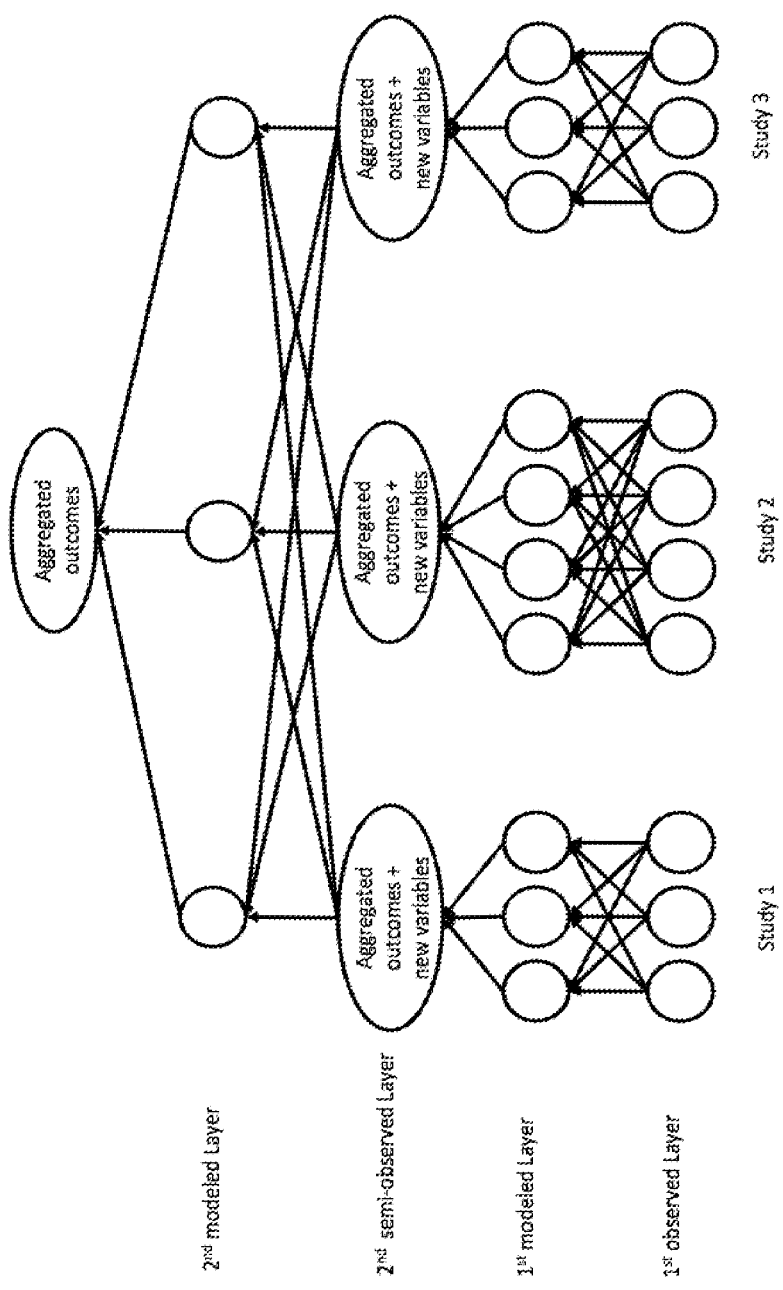
FIG. 4 provides a diagram of a recursive hierarchical similarity based machine learning method in accordance with the present disclosure.

The recursive hierarchical similarity based learning machines of the present disclosure are illustrated by way of example and referring to FIG. 4. In the example shown in FIG. 4, three clinical trials, study 1, study 2, and study 3 are used for the hierarchical similarity based machine learning of the present disclosure. First, the learning machine applies the SB learning methods described to individual patients within each trial to obtain attribute scaling factors and weights, as described. Following application to at the individual patient level, the learning machine applies the SB learning methods described to factor into learning similarities between each of the different trials. Aggregate variables, such as for example, mean outcome, mean age, and proportion of female participants, are introduced to determine the similarities between such aggregate groups across each of the trials, and new variables are often introduced to differentiate and account for differences observed between trials. The learning machine continues to perform the SB learning described at different levels and combines the results of each level of learning to predict how a new patient will perform in the trial.

In the aggregate level, the mean outcome $\overline{O}_t$ for a group/trial t is modeled based on the similarity based machine learning described herein as and predicted outcome is:

$$\overline{Y}_t = \sum_{l=1}^{L} W_{tl} \overline{O}_l \qquad (15)$$

Where $W_{tl}$ is determined by the similarity score $S_{tl}$ between groups t and l using group attributes such as mean age and mean weight as shown in Eq. 2.

The outcome for the i-th person (person of the i-th type) in the t-th trial is denoted by $Y_{ti}$, i=1, 2, ..., K and is predicted by the similarity weighted mean:

$$Y_{ti} = \sum_{l=1}^{L} W_{tl} \sum_{j=1}^{N_l} W_{li,j} O_{lj}, i = 1, 2, \ldots, N_t \quad (16)$$

Where weight $W_{li,j}$ is determined by the similarity $S_{li,j}$ between the i-th subject and the j-th subject in the same l-th trial. That is, the weight is the normalized similarity score derived from Eq. 2.

To determine the attribute scaling factors $R_k$, the error E for the hierarchical recursive learning machine can be defined as:

$$E = \frac{\sum_{t=1}^{L} \sum_{i=1}^{N} (Y_{ti} - O_{ti})^2}{NL} \quad (17)$$

The error term E in either of Eq. 10 or Eq. 13 can be substituted with the error term E in Eq. 17 above, and the attribute scaling factors $R_k$ can then be obtained.

The hierarchical recursive similarity based learning machines described can be advantageously employed even when certain data is unavailable. For example, often individual clinical trial data is unavailable but aggregated results from trials are published. This aggregated information can be used by the learning machines described herein to provide predictions on individuals engaged in another trial. For example, if individual data for one trial is available and the only information available from a second trial is the mean, standard deviation, and sample size, the learning machines of the present disclosure can be directly on the data.

Alternatively, the learning machines disclosed may use the limited information obtained from the second trial by assuming N patients in the trial are identical with the same response and attributes. This data set can be combined with the individual data from the first trial into a single dataset. Additional variables may be included in the dataset. The learning machine can then perform hierarchical recursive similarity based learning on the created training data to provide predictions on how new patients will perform in trials.

The outcome variables in a given training data related to clinical trials may include, but are not limited to, quality of life during trial, disease state after trial, disease state at time T after trial, survival through trial, survival at time T after trial. Thus, the present recursive hierarchical similarity based learning machines described herein may be used to determine a course of treatment for a given disease. The attributes of a new patient not included in the training data may be used in the by the recursive hierarchical similarity based learning machine to predict if the new patient is a candidate for taking a drug that was studied in the clinical trials used as the training data. The learning machine may predict good quality of life, survivability, and disease remission, thus prompting treating with the drug. In contrast, the recursive hierarchical similarity based learning machine may predict poor quality of life and or death from the drug and based on the predicted outcome, the drug may not be administered to the patient.

The invention claimed is:

1. A system for machine learning, the system comprising:
   a computer;
   a non-transitory computer-readable medium having software stored therein, when executed by said computer, performs a machine learning method comprising the steps of:
   generating a similarix from received training data of N subjects, where each subject is defined by a small set of attributes, wherein the small set of attributes is less than or equal to three hundred attributes;
   assigning an initial similarity score to each of the subjects;
   calculating a scaling factor for each attribute;
   generating improved similarity scores using the scaling factors;
   using the improved similarity scores to predict future outcomes for new subjects; and
   wherein the future outcomes are predicted without overfitting to actual, observed outcomes.

2. The system of claim 1, where the system further comprises training data have N sets of input data and a corresponding number of outputs, $O_i$.

3. The system of claim 1, wherein each of the N sets of inputs have k attributes.

4. The system of claim 3, wherein the training data is normalized prior to assigning an initial similarity score to each of the subjects.

5. The system of claim 4, wherein the training data is normalized by the mean and standard deviation of the training data.

6. The system of claim 5, wherein initial similarity scores are assigned by generating a regression model of the training data.

7. The system of claim 6, wherein future outcomes are predicted by calculating the weights of the improved similarity scores.

8. The system of claim 7, wherein the scaling factor is modified in response to receipt of additional training data, attributes $X_{ij}$ and outcome data $O_i$.

9. The system of claim 8, wherein the scaling factor is modified by the optimization method or the gradient method.

10. The system of claim 8, wherein the modified scaling factor is used to calculate modified improved similarity scores.

11. The system of claim 10, wherein the modified improved similarity scores are used to modify the prediction of future outcomes.

12. A method of supervised machine learning, the method comprising the steps of:
    providing training data to a learning machine;
    generating initial similarity scores;
    generating improved similarity scores;
    using the improved similarity scores to model outcome;
    using the modeled outcome to predict future outcomes;
    wherein the training data comprises N subjects defined by k attributes;
    wherein the improved similarity score is calculated by first calculating an attribute scaling factor from the initial similarity scores;
    wherein the k attributes are less than or equal to three hundred attributes; and
    wherein the future outcomes are predicted without overfitting to actual, observed outcomes.

13. The method of claim 12, wherein the attribute scaling factor is modified over time.

14. The method of claim 13, wherein the attribute scaling factor is modified by the gradient method.

15. The method of claim 13, wherein the attribute scaling factor is modified by the optimization method.

16. The method of claim 12, wherein the method can be used recursively at different aggregations using weights at different levels $W_{tl}$ and $W_{lij}$ to predict outcomes.

17. A method for treating a disease in a current patient, the method comprising the steps of:
   providing training data of prior patients in a clinical trial to a learning machine, the training data including for each prior patient attributes and patient outcome,
      generating initial similarity scores between prior patients;
      generating improved similarity scores between prior patients;
      using the improved similarity scores to model patient outcome;
   using the modeled outcome to predict an outcome of a current patient
   using the predicted outcome to arrive at a course of treatment for the current patient and
wherein generating improved similarity scores between prior patients comprises calculating attribute scaling factors from the initial similarity scores and using the calculated attribute scaling factors to generate the improved similarity scores.

* * * * *